United States Patent
Vainshelboim et al.

(10) Patent No.: US 8,034,126 B2
(45) Date of Patent: Oct. 11, 2011

(54) HENNA AND VEGETABLE DYE BASED COMPOSITIONS FOR COLORING OF HUMAN HAIR

(76) Inventors: Alex Vainshelboim, Maple Grove, MN (US); Tatyana Vainshelboim, Maple Grove, MN (US)

( * ) Notice: Subject to any disclaimer, the term of this patent is extended or adjusted under 35 U.S.C. 154(b) by 0 days.

(21) Appl. No.: 12/816,005

(22) Filed: Jun. 15, 2010

(65) Prior Publication Data

US 2010/0313362 A1 Dec. 16, 2010

Related U.S. Application Data

(60) Provisional application No. 61/187,062, filed on Jun. 15, 2009.

(51) Int. Cl.
*A61Q 5/10* (2006.01)
*A61K 8/00* (2006.01)

(52) U.S. Cl. ......... 8/405; 8/435; 8/624; 8/646; 424/70.1

(58) Field of Classification Search .............. 8/405, 435, 8/624, 646; 424/70.1
See application file for complete search history.

(56) References Cited

U.S. PATENT DOCUMENTS

| | | | |
|---|---|---|---|
| 4,183,366 A | 1/1980 | Bartuska et al. | |
| 5,075,102 A | 12/1991 | Hubaud et al. | |
| 5,698,184 A | 12/1997 | Pickart | |
| 6,139,853 A | 10/2000 | Akram et al. | |
| 6,428,580 B2 | 8/2002 | Schultz et al. | |
| 6,696,417 B1 | 2/2004 | Raghupathi et al. | |
| 7,087,255 B2 | 8/2006 | McGrew et al. | |
| 7,186,279 B2 * | 3/2007 | Palpu et al. ........................ 8/405 |
| 7,550,014 B2 | 6/2009 | Greaves et al. | |
| 2001/0042276 A1 | 11/2001 | Kawasoe et al. | |
| 2003/0145395 A1 | 8/2003 | Murakami | |
| 2006/0010618 A1 | 1/2006 | Blecour-Castro et al. | |

FOREIGN PATENT DOCUMENTS

| | | |
|---|---|---|
| DE | 4201749 | 7/1993 |
| DE | 4402203 | 7/1995 |
| DE | 19600225 | 7/1997 |
| JP | 4013611 | 1/1992 |
| JP | 4164018 | 6/1992 |
| WO | 2007130777 | 11/2007 |

OTHER PUBLICATIONS

Aminuddaulah Abul Farj Ibn Al-QuffMascehi; Kitaab-al-'Umdah-fil-Ieraahat, Part II (13th century ADI, Dayerah-al- Ma'aarif Usmania, Hyderabad, 1937 AD p. 63-64. English Translation including Terminology Conversion (TKDL Extracts).
Mohammad Shareef Khan; Daaj-al-Amraaz (18th century AD), Afzal-al- Matabe, Barqi Press, Delhi, 1921 AD p. 330. English Translation including Terminology Conversion (TKDL Extracts).
Mohammad Najmul Ghani Khan; Qaraabaadeen Najm-al-Ghani (20th century AD), Munshi Nawal Kishore, Lucknow, (Second Edition) 1928 AD p. 175. English Translation including Terminology Conversion (TKDL Extracts).
Abu Ali Ibn-e-Sina: Al-Qaanoon-fil-Tibb, vol. II (IIth century AD), Institute of History of Medicine and Medical Research, Jamia Hamdard, New Delhi-62, 1987 AD p. 147. English Translation including Terminology Conversion (TKDL Extracts).
Mohammad Azam Khan; Muheet Azam vol. II ( Part II) (19th century AD), Matba Nizami, Kanpur, 1898 AD p. 61. English Translation including Terminology Conversion (TKDL Extracts).
Mohammad Azam Khan; Muheet-e-Azam vol. IV (Part I) (19th century AD), Matba Nizami, Kanpur, 1899 AD p. 49. English Translation including Terminology Conversion (TKDL Extracts).
Charles Zviak, The Science of Hair Care, Marcel Decker.1986, 235-240.
Charles Zviak, The Science of Hair Care, Marcel Decker.1986, 240-245; 415-420.
Joseph Rivlin, The Dyeing of Textile Fibers, Theory and Practice, PCT&S, Philadelphia, 1992,30-52; 108-109.
H.S. Freeman & A.T. Peters, Colorants for Non-Textile Applications, Elsevier, 2000, pp. 382-449.
Paul Coats , Encyclopedia of Dietary Supplements, 2005, Marcel Decker, pp. 133-141.
R. Hurrel, How to Ensure Adequate Iron Absorption from Iron-fortified Food, Nutrition Reviews, vol. 60,7 pp. 7-13, Jul. 2002.
Miller D.D. , An in Vitro Method for Estimation of Iron Availability from Meals, The American Journal of Clinical Nutrition, 34(10), pp. 2248-2256, Oct. 1981.
Fischer at all., Removal of Heavy Metals from Soil Components and Soil by Natural Chelating Agents., Water, Air and Soil Polution 138, p. 271, 2002.
A. Hunting, Encyclopedia of Shampoo Ingredients, Micelle Press,1983, pp. 240-243; 319-323.

* cited by examiner

*Primary Examiner* — Eisa Elhilo
(74) *Attorney, Agent, or Firm* — Myers Wolin, LLC

(57) ABSTRACT

New, effective and non-toxic compounded henna based hair dyes that are non-toxic, natural and hypoallergenic that provide an alternative to conventional hair color. The products are made using 100% Green Chemistry and do not utilize encapsulation.

25 Claims, No Drawings

HENNA AND VEGETABLE DYE BASED COMPOSITIONS FOR COLORING OF HUMAN HAIR

CROSS REFERENCE TO RELATED APPLICATIONS

The present application claims the benefit of U.S. Patent Application No. 61/187,062, filed Jun. 15, 2009, the contents of which are incorporated herein by reference.

BACKGROUND OF THE INVENTION

For centuries the use of hair coloring was restricted to the fashion needs of a privileged few and was dictated by necessity to hide gray hair. Today a lot of people, both women and man, use hair coloring to change their appearance. There are several reasons for this: to hide white hair, to lighten hair color and add additional highlights, to remove the yellow look from grey hair, enhance natural color, etc.

From a technical standpoint, extensive laboratory and research work is essential because of the diverse problems to be solved. The indiscriminate use of certain colorants may have dermatological and toxicological side effects. It is well known that hair dyes are subject for large studies in the field of allergology. Specific classes of dyes like direct and oxidative dyes, also known as Paraphenilene Diamine dyes, are known allergens and suspected carcinogens and genotoxins. (Charles Zviak, The Science of Hair Care, Marcel Dekker, 1986, p.235-240).

Although hair coloring using natural dyes is mentioned in most ancient documents, the development of new natural plant based hypoallergenic hair coloring systems remains a scientific and technological challenge. Most common are hair dye compositions based on henna. According to Zviak, henna is a natural product and generally does not have any side effects. The henna leaves are dried and crushed into powder and applied as a paste with hot water. Henna is typically produces auburn and brown-orange colors. However, henna does have a number of major drawbacks, such as complicated preparation and application, unleveled shades, incompatibility with other hair dyes and treatments, etc. Therefore, henna was almost completely replaced with synthetic hair dyes.

Recently henna has been regarded as a "back to nature" alternative for home use and by many hairdressers.

As early as 1907 improvements in henna dyes were attempted and were based on hair lacquers using phenol compounds such as pyrogallol and nickel, iron, copper, cobalt, or lead salts in the presence of reducing salt and a medium containing henna. These compounds produced full range of colors.

However, the disadvantages of hair dyes containing metallic salts are numerous. Most of them are toxic to some extent, and their use is strictly regulated. They nearly always create a dull, leaden color with a flat metallic appearance. Moreover, the metal fixed on the hair shaft acts as a catalyst, causing an abrupt breakdown of the hydrogen peroxide in bleaching products or permanent wave fixers resulting in significant hair damage (C. Zviak, p. 241). Compounded henna remains the only natural alternative to conventional hair color.

Therefore, development of new non-toxic natural hypoallergenic alternatives to conventional hair color remains a scientific and technological challenge. Discovery of mild, non-toxic ingredients for compounded henna compositions can theoretically solve problems of color appearance, toxicity, application, and compatibility with other treatments.

The patent literature describes the enhancement of conventional oxidative dye composition with henna (or enhancement of so-called black henna). In U.S. Pat. No. 6,139,853, the solid hair colorant composition described comprises a 10-35% p-phenilenediamine based oxidative formula also containing non-oxidative dyes like HC Blue 2 and HC Yellow 12 and 25-70% neutral henna. While the disclosed colorant contains henna and is more convenient to use in comparison to regular henna, it still contains p-phenilenediamine that is not suitable for people with allergic reactions to p-phenilenediamine.

A similar composition, described in US 20060010618, discloses Myristine Africana plant parts used in an oxidative (p-phenilenediamine) based formula.

DE4402203 describes hair dyeing compositions containing ginseng and plant based dye as a temporary color.

JP4013611 A2 describes a hair coloring composition based on freeze-dried plants such as Acacia Shikouka and mordanting metals like Fe, Cr, Mn, or Sn.

JP2872385 B2 describes combination of oxidative dyeing agent, vegetable dyeing agent and quaternary ammonium salt.

A similar composition is described in U.S. Pat. No. 4,183, 366 where 75-95% henna powder is mixed with non-ionic surfactant and 0.5-5.0 of a quaternary salt. Both patents describe a more convenient application procedure. However, there is no mention of durability and/or coloring palette improvement.

DE4201749 A1 describes compositions utilizing Alkanna root but only for graphite gray color.

DE19600225 A1 describes hair dyeing compositions based on utilization of oils and liquid waxes in a mixture of natural and synthetic dyes.

WO2007130777 A3 describes a composition of Acid Blue 74 and Mordant Red11 and combination of encapsulated mordant and natural dye extract. This composition does not seem to be practical due to low core payload possible because of the encapsulation technique.

US20030145395 describes hairdressing compositions of henna, tannin, catechin, gardenia, lac, annatto, brazilin and turmeric based pigments providing wide range of colors. However, the mordants described in this patent, like white lead and antimony white, can possess toxicological risks. Also, the scalp staining is the probable cause of using titanium and zinc oxides to inhibit the coloring process.

U.S. Pat. No. 7,186,279 describes a black dye comprising of Juglas Regia, Indigofera Tinktoria, Acacia Accocina, Lawsonia Interims, and hair coloring mordant based on natural tannins. While the composition is described as nontoxic and safe, it results in only one color—black, which is not practical for the modern hair coloring industry.

The use of mordants is well known in the leather and textile industry and has been employed for centuries as a vegetable dye coloring method. However, the use of mordants has been limited in recent years because of their generally high toxicity. The most common mordants are salts of chromium and are still used in the leather industry, although rarely. Other mordants include salts of aluminum and copper which also possess both toxicological and environmental concern (Joseph Rivlin, The Dyeing of Textile Fibers, PCT&S, Philadelphia, 1992, p. 30-52, H.S. Freeman & A.T. Peters, Colorants for Non-Textile Applications, Elsevier, 2000, pp. 382-449) but are still in use in some textile and leather applications.

The mordant's function is to form a complex between a polyvalent metal salt and a dye. The application of a mordant traditionally requires at least two steps and often includes a pre- or post treatment as well. The reaction between mordants and dyes is virtually instantaneous, making it necessary to apply them separately. This is a significant disadvantage of the mordanting technique because scalp staining can occur due to the fast reaction between mordant and dye.

A desirable quality to incorporate into a mordant-dye system for coloring human hair would be to provide time delay in this reaction for several reasons. First, to decrease scalp staining which occurs during the instantaneous reaction between dye and mordant on both scalp and hair. Second, to make the system more convenient and give stylist or home user an opportunity to adjust the color and its depth. Third, to save time and make this application as convenient as a regular hair coloring process.

Copper sulfate has been known as a mordant for centuries. Its limitations of application in industries like textiles are limited due to harmful ecological effects (Rivlin p. 108-109) and toxicity. For the same reasons, copper sulfate did not find applicable use in hair coloring applications. However, copper based or mordanted dye compositions applied on textiles exhibit valuable qualities like broad range of colors, light and weather fastness and durability of color (Rivlin p. 108-109).

However, some copper salts such as lactic, acetic, tartaric, succinic and gluconic acids, in particular ones made from renewable plant based sources, are not only considered to be non-toxic but are also used as a dietary and food supplements. Copper is involved in numerous biochemical reactions in human cells and is a component of multiple enzymes, is involved with the regulation of gene expression, mitochondrial function/cellular metabolism, connective tissue formation, as well as the absorption, storage, and metabolism of iron.

Copper levels are tightly regulated in the body. Copper deficiency can occur in infants fed only cow-milk formulas (which are relatively low in copper content), premature/low-birth weight infants and in adults causing cystic fibrosis. Medicinal use of copper compounds dates to Hippocrates in 400 B.C. Bacterial growth is inhibited on copper's surface, and hospitals historically installed copper-alloy doorknobs and push-panels as a measure to prevent transmission of infectious disease. (Paul Coates et al., Encyclopedia of Dietary Supplements, 2005, Marcel Decker, pp.133-141).

The direct application of copper salts of lactic, acetic, tartaric, maleic, glycinic, succinic and gluconic acids in natural henna based compounding is not found in the art.

U.S. Pat. No. 7,087,255 discloses copper salts application in chewing gums as a dietary supplement, in particular copper gluconates and lactates. Copper Gluconate is disclosed as a suntan accelerator and skin protectant during sun tanning (U.S. Pat. No. 5,075,102). Similar application is described in U.S. Pat. No. 5,698,184. Copper Gluconate was proposed to increase melagenesis (darkening of skin and hair) as a part of sun tanning composition as an alternative to DHA (U.S. Pat. No. 6,696,417). U.S. Pat. No. 6,428,580 describes use of Copper Gluconate as a part of oxidizing system for perms.

Hair dyes known as dry henna (compounded henna) contain metallic salts in order to provide a right color. Most salts are heavy metals. Most of them are toxic to some extent, and their use is strictly regulated. Compounded henna nearly always creates a dull, leaden color with a flat metallic appearance. Despite all the detriments, compounded henna remains to be the only natural alternative to conventional hair color.

U.S. Pat. No. 7,550,014 entitles "Composition for dyeing keratin fibers and a method of dyeing hair using same" is limited to encapsulation and one part system only.

Copper Gluconate is mentioned but it is known that encapsulation of water soluble salts is very difficult and in many cases impractical. The maximum theoretical payload of encapsulated material can be no more than 10%.

Active copper content in Copper Gluconate can not be more than 12.4% based on molecular weight. In order to achieve concentrations mentioned in this patent (0.01-5%) the disclosed formula has to contain 620% of Copper Gluconate encapsulated to obtain 5% of active copper. It is impossible since maximum concentration of ingredients in formula can be only 100%. At 50% of encapsulate in formula there is 0.4% of active copper and there is not enough room for other ingredients, i.e. water as it is known that aqueous dyes can not produce color without sufficient water.

At 5% of encapsulate in the formula of this patents composition, the composition can deliver only 0.04% of active copper. At this concentration, color can not be developed due to very low concentration of mordant, i.e. Copper Gluconate. Practical concentrations around 0.5-5% of active copper cannot be achieved by encapsulation techniques.

Therefore, development of a non-toxic natural hypoallergenic alternative to conventional hair color which does not exhibit these detrimental effects remains a scientific and technological challenge and it is an object of this invention to provide a hypoallergenic alternative to conventional hair color which does not exhibit these detrimental effects.

Therefore, it is an object of this disclosure to provide final products that can be made using 100% Green Chemistry.

It is an object of this disclosure to provide final products that do not utilize encapsulation.

It is an object of this disclosure to provide new, effective and non-toxic compounded henna based hair dyes.

SUMMARY OF THE INVENTION

One advantage of this invention is that the final products can be made using 100% Green Chemistry.

Another advantage is that is that encapsulation is not utilized.

This invention relates to new, effective and non-toxic compounded henna based hair dyes.

A new mechanism using 100% Green Chemistry for swelling of keratin fiber using 100% natural and completely renewable and sustainable dye composition at pH 4.5 and lower than isoelectric point of keratin was discovered. Using all natural ingredients such as Natural Benzyl Alcohol, Benzylaldehyde as dye carrier and Natural Propanol as a solvent, and salts of natural assets it was possible to create a mechanism of ligand binding of human hair with natural dye. Natural Benzyl Alcohol in combination with Natural Propanol and acid causes human hair internal swelling and shifting of micro fibrils mostly in cortex area. This swelled fiber at pH lower than isoelectric point (pH 4.5) has high free volume and abundance of active groups. The ligand binded polynucleous complexes with hair keratin enabled the creation of all natural hair dye compositions that possess very unique qualities of these technologies that could previously be achieved only by using synthetic and/or oxidative dyes.

The invention is based on specific properties of copper like salts to promote ligand interaction with the polymeric matrix and other ligand donors like dyes. It was determined that copper complexes can be distributed as particles in the fibrous material. It was elucidated that most of the copper particles are capable of forming poly-nucleus complexes with fibrous materials. The type of copper based complex highly depends on type of fiber, polymeric matrix and conditions of particular treatment. These poly-nucleus complexes form a stable structure with polymeric matrix with compensated spin and can disassociate to smaller formations and react with other ligands.

Compounded henna concentrate can be made by mixing and/or heating its compounded ingredients with acid and natural co-solvent such as vegetable Glycerin, Propanediol (from corn), and other natural glycols and poly-alcohols. This process enables compounded henna to act as a dye concentrate. This dye concentrate, when added to conventional formulations such as gels, emulsions, suspensions, sprays at pH lower than 4.5 (isoelectric point of keratin) and/or mixed together with all natural binding system at pH 4.5 and lower will produce permanent coloring with necessary delay. This dye concentrate at pH 4.5 and lower can be added to conventional formulations such as gels, emulsions, suspensions, sprays at pH lower than 4.5 (isoelectric point of keratin) and act as a direct dye coloring system for human hair even in the absence of mordant.

This combination of all natural ligand binding system and all natural henna at pH lower than 4.5 can be formulated with dietary salts of copper and other dietary salts. This composition is based on ligand binding of self chelating salts of copper, such as Copper Gluconate and other copper salts with hair keratin. This ligand based complex forming system is employed to carry high payload of color delivering ingredients such as Henna. The color delivering ingredients, i.e. natural dyes and color containing actives such as antioxidants, antimicrobials and other phyto-therapeuticals; vitamins and co-enzymes; bioflavonoids, flavonoids, isoflavonoids, neoflavonoids can also have coloring properties.

The self chelating properties of some copper salts provide necessary inhibition and/or short delay in the reaction that makes application convenient and extremely practical. Color deposition does not occur on the scalp, only on hair and can be applied at home and/or salon.

It is the first time that Natural Benzyl Alcohol from Cashew oil or oil of Bitter Almond is applied to hair coloring formulations. Natural Benzyl Alcohol is one of the major dye carriers without which the performance of hair color is very limited.

In experiments it was also determined that Benzaldehyde that can be made from oil of Bitter Almond that commonly used as a flavor or fragrance ingredient and never before was used as a hair coloring carrier, can be used as a carrier of dyes in natural formulations.

Other ingredients that can be used such as Natural Propanol and gluconic salts can be made from corn and completely renewable and never had before been used in hair colorings compositions.

With these elements of green chemistry, a new mechanism was discovered for swelling of keratin fiber using 100% natural and completely renewable and sustainable dye composition. Using all natural ingredients such as Natural Benzyl Alcohol, Benzylaldehyde as dye carriers and Natural Propanol as a solvent, and salts of natural acids it was possible to create a mechanism of ligand binding of human hair with natural dye.

Natural Benzyl Alcohol in combination with Natural Propanol and natural acid and it salts causes human hair internal swelling and shifting of micro fibrils mostly in cortex area. This swelled fiber at pH lower than isoelectric point (pH 4.5) has high free volume and abundance of active groups.

The ligand binded polynucleous complexes with hair keratin enabled the creation of all natural hair dye compositions that possess very unique qualities of these technologies that could previously be achieved only by using synthetic and/or oxidative dyes.

These qualities are mixable shades, high resistance of product to environmental conditions and cumulative effects. This same mechanism also enables the control of a diffusion of dye which also resulted in extended gray coverage, reduced scalp staining and possibility of applying hair color without hair damage and using conventional application tools.

This specification discloses compositions of all natural non-toxic, non-allergenic henna based dyes. It can be formulated with dietary salts of copper and other dietary salts. This composition is based on ligand binding of self chelating salts of copper, such as Copper Gluconate and other copper salts with hair keratin. This ligand based complex forming system is employed to carry high payload of color delivering ingredients such as Henna. The color delivering ingredients, i.e. natural dyes and color containing actives such as antioxidants, antimicrobials and other phyto-therapeuticals; vitamins and co-enzymes; bioflavonoids, flavonoids, isoflavonoids, neoflavonoids can also have coloring properties.

The self chelating properties of some copper salts provide necessary inhibition and/or short delay in the reaction that makes application convenient and extremely practical. Color deposition does not occur on the scalp, only on hair and can be applied at home and/or salon.

Along with these properties, some other advantages of these compositions are described, such as: stability enhancement, in particular of iron salts that are also responsible for color development, better color deposition on human hair, less scalp staining, better durability, etc.

Some copper salts, in particular those derived from renewable plant based sources like lactic, acetic, tartaric, succinic and gluconic acids, are not just considered to be non-toxic but are also used as dietary and food supplements. Copper is involved in numerous biochemical reactions in human cells.

A key success factor for natural, alternative, nontoxic, hypoallergenic and high performance hair coloring composition is to develop new compounds of henna with non-toxic complexes to create a broad dye coloring palette.

An all natural non-toxic non-allergenic henna based compound is formulated with the dietary salts that can be used as a non toxic mordants or complex forming agents for ligand copper binded plant based henna based hair dye compositions containing at least one copper ligand donor, other mineral salts, natural dyes and color contained actives such as antioxidants, antimicrobials and other phyto-therapeuticals, vitamins and co-enzymes, bioflavonoids, flavonoids, isoflavonoids, neoflavonoids.

DETAILED DESCRIPTION

The copper compound may be selected from, for example, Copper Lactate, Copper Gluconate, Copper Acetate, Copper Glycinate, Copper Acetate, Copper Lysine, Copper Tartrate, Copper Salicylate, Copper Succinate.

Other mineral salts selected from but not limited to the following group are also useful in the present invention: Ferrous Lactate, Ferrous Gluconate, Ferrous Fumarate, Ferrous Citrate, Ferric Ammonia Citrate, Zinc Lactate, Zinc Citrate, Zinc Picolinate, Zinc Tartarate, Potassium Gluconate, Potassium Citrate, Potassium Lactate, Potassium Citrate, Potassium Succinate, Potassium Chloride, Calcium Maleate, Magnesium Citrate, Magnesium Carbonate, Magnesium Oxide, Calcium Gluconate, Calcium Citrate, Calcium Carbonate, Manganese Gluconate, Manganese Glycinate, Selenium Selenomethionine.

Copper salts that are listed above are typically do not have a stability problems. As matter of fact an application of copper salts is one of the best ways to increase light stability but in comparison with iron salt on the compositional mordanting it is very difficult to get dark shades like dark brown and black using a copper salts as a mordant alone (Rivlin, p. 108-109).

Natural Dyes and Color Contained Actives (antioxidants, antimicrobials and other phyto-therapeuticals) may be selected from Henna, Acacia Dealbata Flower/Stem Extract, Annatto, Anthocyanins, Astaxanthin, Betanin, Capsanthin/Capsorubin, Carotenoids, Chlorophyll, Coptis Japonica Rhizome Extract, Crocus Sativus Flower Extract, Curcuma Longa, Turmeric Extract, Dunaliella Bardawil Powder, Gardenia Florida Fruit Extract, Gardenia Jasminoides Fruit Extract, Guaiazulene, Carthamin, Rosa Hybrid Flower Extract, Rubia Cordifolia Root Extract, Rubia Tinctorum Root Extract, Purpuroxanthin, Morindanigrin, Morindadiol, Rhubarb Extract, Purpurin, Pseudupururin, Morindone, Emodin, Crocin, Crocetin, Canthaxanthin, Sorghum Vulgare Seed/Skin/Stalk Extract, Vitis Vinifera (Grape) Fruit Powder, Vitis Vinifera (Grape) Skin Extract, Wine Extract, Deoxysantalin, Atromentin, Humin, Berberine.

Vitamins and Co-enzymes may be selected from Beta Carotene, D-Alpha Tocopherols, Co Enzyme Q-10, D-Biotin, Folic Acid, Niacin, Niacinamid, Riboflavin, Tocopherol, Vitamin A, B1, B2, B5, B6, B12, D3.

Bioflavonoids, flavonoids, isoflavonoids, neoflavonoids may be selected from Flavone, Luteolin, Apigenin, Baicalein, Rutin, Acacetin, Fisetin, Kaempferol, Myricetin, Quercetin, Naringenin, Hesperidin, Taxifolin, Genistein, Genistin, Daidzein, BiochaninA, Doxorubicin, Quercetin, Kaempferol, Myricetin, Fisetin, Isorhamnetin, Pachypodol, Rhamnazin, Eriodictyol, Homoeriodictyol, Tangeritin, Dihydrokaempferol, Glycitein, Catechins, Epicatechins, Morin, Brazelin, Brazilein, Haematein, Haematoxylon, Atrocappanon, Fukugetin, Datiscetin, Rhamnocitrin, Rhamnetin, Xanthorhamnin, Gossypetin.

The above salts are used as nutrition supplements, vitamin complexes and for fortification of food. In many cases compatibility and stability of their ligand complexes in particularly in aqueous media is in question.

As an example, most of the iron supplements with high bioavailability are susceptible to oxidation and reaction with other ingredients during storage. During oxidation, the ferrous form Fe (2+) is converted to ferric form Fe (3+) that can cause precipitation. (U.S. Pat. No. 7,087,255; R. Hurrel, How to ensure Adequate Iron Absorption from Iron-fortified Food, Nutrition Reviews, Vol.60,7 pp 7-13 and Miller DD et all., An in vitro method for estimation of iron availability from meals, The American Journal of Clinical Nutrition, 43(10),pp2248-2256). Thus, it makes application of any liquid composition of ferrous salt in personal care products difficult due to stability requirements. In particular, the development of liquid hair coloring composition containing just Ferrous Gluconate would be impractical due to the stability concern. The typical required shelf life of hair coloring product should be at least 12 month. Attempt to stabilize ferrous salt is described in WO 2007/130777A3 by means of encapsulation. While encapsulated Ferrous Gluconate can make it more stable, the payload of encapsulate is typically low. The shell material and encapsulation process itself is expensive, elaborate and time consuming. This makes the technology of hair coloring product very expensive and impractical.

Several hydrocolloid based acidic formulations were made using both copper salts and iron salts and its compositions. All compositions were subjected to the long term standard ambient and light stability protocol as well as accelerated stability (Table 1). Hydrocolloids containing 10% of Copper and Iron Gluconates were prepared and mixed proportionally from 0-10%.

TABLE 1

Stability assessment of Iron and Copper Gluconates combinations:

| | Copper vs. Iron Gluconate % proportion | | | | | | |
|---|---|---|---|---|---|---|---|
| | 0:10 | 2:8 | 4:6 | 5:5 | 6:4 | 8:2 | 10:0 |
| Stability 1 month | failed | stable | stable | stable | stable | stable | stable |
| Stability 2 month | failed | stable | stable | stable | stable | stable | stable |
| Stability 6 month | failed | stable | stable | stable | stable | stable | stable |
| Stability 8 month | failed | stable | stable | stable | stable | stable | stable |
| Accelerated Stability 1 week | stable | stable | stable | stable | stable | stable | stable |
| Accelerated Stability 30 days | failed | stable | stable | stable | stable | stable | stable |
| Accelerated Stability 60 days | failed | stable | stable | stable | stable | stable | stable |

Combinations of Ferrous Lactate and Copper Gluconate show similar pattern although Ferrous Lactate compositions are less stable and require more Copper Gluconate to stabilize them.

Table 1 discloses the following unexpected results. All of the Ferrous Gluconate and Ferrous Lactate compositions showed precipitation and typical Fe (3+) dark brown water like face separation on the top. The addition of as little as 2.0% copper dietary salt (Copper Gluconate) kept this composition stable for at least 8 months under normal conditions and for 60 days at accelerated conditions.

Another unexpected result occurred when color and mordanting compositions were mixed together and left still for 30 minutes (typical time of application of hair color). The dark brown compounded henna ("Dark Brown Henna") was made with one of the ingredients from classes of ingredients described in the Scope of Invention.

Preparation is similar to that described in US20030145395. Precipitation occurred almost instantaneously in the compositions containing Ferrous Gluconate and Ferrous Lactate alone (without Copper salt addition). The samples mixed with equal amounts of Copper salts even as low as 10% have showed no precipitation on the course of 30 min and more as set forth in Table 2.

TABLE 2

Precipitation of Copper and Iron Gluconate hydrogels with "Dark Brown Henna"-30 minute test.

| | Copper vs. Iron Gluconate % (of 100% total) proportion | | | | | | |
|---|---|---|---|---|---|---|---|
| | 0:100 | 10:90 | 30:70 | 50:50 | 70:30 | 90:10 | 100:0 |
| Precipitation | Yes | No | No | No | No | No | No |

Color was applied on DeMeo Brother's Natural White Hair Swatches and on volunteers as a comparative ¼ head scalp surface test. A portion of the swatches was subjected to outdoor weather and a durability test for 45 days. All samples were evaluated for color in comparison with initial colored swatches using the same conditions.

TABLE 3

"Dark Brown Henna" using ligand binded Copper at 45 C. for 45 min.

| | Copper Gluconate vs. Iron Gluconate % (of 100% total) proportion | | | | | |
|---|---|---|---|---|---|---|
| | 0:100 | 10:90 | 30:70 | 50:50 | 70:30 | 90:10 | 100:0 |
| Deposition | Poor | Fair | Good | Good | Good | Good | Fair |

| | Copper Lactate vs. Iron Gluconate % (of 100% total) proportion | | | | | |
|---|---|---|---|---|---|---|
| | 0:100 | 10:90 | 20:80 | 50:50 | 60:40 | 80:20 | 100:0 |
| Deposition | Poor | Fair | Good | Good | Good | Fair | Fair |

As demonstrated by the results set forth in Table 3, best results on color deposition can be achieved within presence of copper salts like Copper Gluconate and Copper Lactate. Iron Gluconate was noted to exhibit poor deposition. Best results were achieved in proportion 30:70 parts of Copper salt.

TABLE 4

Scalp staining. Comparative evaluation

| | Copper vs. Iron Gluconate % (of 100% total) proportion | | | | | |
|---|---|---|---|---|---|---|
| | 0:100 | 10:90 | 30:70 | 50:50 | 70:30 | 90:10 | 100:0 |
| Staining | Heavy | Moderate | Mild to Moderate | Mild | Mild | Very Mild | Very Mild |

As a shown in Table 4 some salts exhibit heavy scalp staining This staining can be eliminated by small addition of a copper salt. Significant improvement was observed from adding as low as 10 parts of copper salt.

TABLE 5

Combined weather and durability test: length 45 days, temperature 45-70 F., medium sun. Hair was shampooed with a mild shampoo every other day.

| | Copper Gluconate vs. Iron Gluconate % (of 100% total) proportion | | | | | |
|---|---|---|---|---|---|---|
| | 0:100 | 10:90 | 30:70 | 50:50 | 70:30 | 90:10 | 100:0 |
| Discoloration | Heavy | Moderate | Mild | Very Mild | Very Mild | Very Mild | Very Mild |

| | Copper Lactate vs. Iron Gluconate % (of 100% total) proportion | | | | | |
|---|---|---|---|---|---|---|
| | 0:100 | 10:90 | 30:70 | 50:50 | 70:30 | 90:10 | 100:0 |
| Discoloration | Heavy | Moderate | Mild to Moderate | Mild | Very Mild | Very Mild | Mild |

| | Copper Acetate vs. Iron Gluconate % (of 100% total) proportion | | | | | |
|---|---|---|---|---|---|---|
| | 0:100 | 10:90 | 30:70 | 50:50 | 70:30 | 90:10 | 100:0 |
| Discoloration | Heavy | Moderate | Moderate | Mild | Very Mild | Very Mild | Mild |

In all cases heavy discoloration was observed buy using an iron salt. Addition of copper significantly improved weather resistance and durability of color.

Self Chelating Properties of Copper Gluconate.

The above described properties of copper gluconates, lactates, and succinates act as natural chelating agents. Some of the chelating properties of D-gluconic acid were described in publication on removal of heavy metals (K. Fisher at. all Removal of Heavy Metals from Soil Components and Soils by Natural Chelating Agents., Water, Air and Soil Pollution 138, 271, 2002). These properties of gluconates, lactates, and succinates and poly-nucleus complexes that disassociate to smaller formations and react with other ligand can possibly explain anomaly in behavior of copper salts in henna based compounding formulations.

To illustrate this fact the following experiment was performed. Copper salts of other acids—Copper Sulfate, Copper Chloride and Copper Acetate, were used in preparation of mordanting solution. Also, two commonly used chelating agents were used—Turpinal SL (Solutia)-Etidronic Acid and Versenol 120—EDTA (Dow Chemical). These chelating agents were used at a concentrations range of 0.09-2.0% to the gel based formula of mordant which than was applied on hair with the same "Dark Brown Henna" dye composition. The surprise was that there was no color deposition in any of the cases using chelating agents, even at low concentration of 0.09%. See Table 6.

TABLE 6

Influence of different copper salts and chelating agents on color deposition

| | Copper salt & Chelating agent, % | | | | | |
|---|---|---|---|---|---|---|
| | Copper Gluconate | Copper Sulfate 0.09-2.0%% Versenol | Copper Chloride 0.09-2.0%% Versenol | Copper Acetate 0.09-2.0%% Versenol | Copper Sulfate 0.09-2.0%% Turpinal | Copper Sulfate 0.09-2.0%% Turpinal | Copper Sulfate 0.09-2.0%% Turpinal |
| Color Deposition | YES | NO | NO | NO | NO | NO | NO |

Influence of Acid Type.

One of the surprising aspects of these findings was selectivity of the process involving "Dark Brown Henna" to a specific acid or acid type.

In most of the cases the use of acid is limited to pH adjustment. The most unexpected result was received on several experiments with different acids added to "Dark Brown Henna" formulas. The following acids were tested: Citric, Glycolic, Lactic and Acetic. The results are listed in Table 7. Surprisingly we found that similar acid types can have different influence on color deposition.

TABLE 7

Influence of acids on color deposition

| Acid, % | Lactic 0.5-5.0% | Glycolic 0.5-5.0% | Acetic 0.5-5.0% | Citric 0.5-5.0% |
|---|---|---|---|---|
| Color Deposition | Good | Good | Moderate | Very Low |

As shown in Table 7, the strongest color can be achieved by using Lactic and Glycolic acids. Acetic Acid produced a weaker color. Citric Acid showed an extremely weak color deposition. It was also completely unexpected that solution of Citric Acid can be used to remove stains from skin.

Citric and Lactic Acids were used in comparison with a typical mix of 10% nonionic surfactant, 25% of alcohol, 5% of acetone, and 60% water, that is used for cleaning color stains from skin. According to the results, Citric Acid is more effective in removing stains of henna based colorant from skin than Lactic Acid or typical stain removal mix.

Citric acid can be used in concentration of 0.5-10% as a stain remover as shown in Table 8.

TABLE 8

Removing stains using different acids and solvent-surfactant system

| | Type of stain remover vs. concentration | | | |
|---|---|---|---|---|
| | Surfactant-solvent mix | Lactic Acid 0.5-5.0% | Acetic Acid 0.5-5.0% | Citric Acid 0.5-5.0% |
| Stain Dark Brown | Not removed | Partially removed | Partially removed | Completely removed at 3.0% |
| Stain Red Brown | Not removed | Partially removed | Partially removed | Completely removed at 5.0% |
| Stain Yellow Brown | Not removed | Partially removed | Partially removed | Completely removed at 5.0% |

Influence of Combination of Acid and Alcohol.

Alcohols as solvents are employed in some hair coloring applications with and without mordant or salt. For example, in US 2001/0042276 A1, an application of dye, metal salt, and alcohol is described. In this particular case, the use of alcohol with synthetic CI Acid Dyes resulted in slowing rate of reaction between dye and protein (hair and scalp/skin). CI Acid Dyes are designed to dye keratin fibers at low pH. This reaction is extremely fast in acidic conditions and therefore scalp and skin stains can occur. A slow down reaction is generally recommended for leveling of color. While most vegetable dyes and henna are generally have no affinity to hair, the use of alcohol and acid combination has a purpose to increase color deposition on human hair. In US20030145395, the pH range from 2.0 to 6.0 is implied with henna compounding. However, there is no mention of use of alcohol of any kind and/or ligand binded cooper as a complex forming system.

Color deposition was measured on DeMeo Brothers Natural White hair. "Dark Brown Henna" color was prepared using the following solvents (some of them can be natural and made from the renewable sources):

Methanol, Ethanol, Propanol, Isopropanol, Butanol, Amyl Alcohol

These alcohols were used with following acids: Lactic, Glycolic, Citric, and Acetic. Dye and Cupper Gluconate based mordant were shaken together and applied on hair. The results are in Table 9.

TABLE 9

Influence of alcohol type and acid on color deposition.

| Composition of acid type vs. type of alcohol | Methanol | Ethanol Natural | Propanol Natural | Amyl Alcohol Natural | Isopropyl Alcohol | Butanol Natural |
|---|---|---|---|---|---|---|
| Dye + Lactic | Light Brown | Light Brown | Dark Brown | Light Brown | Dark Brown | Dark Brown |
| Dye + Glycolic | Light Brown | Light Brown | Dark Brown | Light Brown | Dark Brown | Light Brown |
| Dye + Citric | Low to none | Low to none | Low to none | Low to none | Low to none | Low to none |
| Dye + Acetic | Low to none | Low to none | Light Brown | Low to none | Light Brown | Low to none |

As shown in Table 9, the influence of alcohol on color deposition is selective and the best performance is (in descending order): Propanol, Butanol, Isopropyl Alcohol, Amyl, Ethanol and Methanol.

Influence of Solvent and Co-Solvent.

Co-solvents are an important part of hair coloring formulation. Typical co-solvents are Glycerin, Propylene Glycol, Butylene Glycol (A. Hunting, Encyclopedia of Shampoo Ingredients, Micelle Press, 1983, pp 240-243; 319-323). Another co-solvent for hair coloring applications is Propanediol from corn by DuPont.

Table 10 shows the results of co-solvent influence on hair color deposition of henna based formulations in different color shades.

TABLE 10

Influence of co-solvent type and acid on color deposition.

| Composition of acid type vs. type of co-solvent | Propylene Glycol | Glycerin Vegetable | Propanediol From Corn | Glycerin/ Propanediol 50:50 | Butylene Glycol |
|---|---|---|---|---|---|
| Dye + Lactic | Light Brown | Dark Brown | Light Brown | Dark Brown | Dark Brown |
| Dye + Glycolic | Light Brown | Dark Brown | Light Brown | Dark Brown | Light Brown |
| Dye + Citric | Low to none | Low to none | Low to none | Low to none | Low to none |
| Dye + Acetic | Low to none | Light Brown | Low to none | Light Brown | Low to none |

As shown in Table 10, best results can be achieved by using Glycerin and Propanediol or its mixture with Lactic or Glycolic Acids.

Dye Concentrates

A totally unexpected result was obtained by mixing and heating compounded henna with acid and co-solvent as shown by the results recorded in Table 11. This process enables compounded henna to act as a dye concentrate for permanent and semi-permanent natural hair coloring products. These dye concentrates, when dispersed in water and/or water based formulations such as gels, emulsions, suspensions, shampoos and conditioners. An example of compounded henna dye concentrate is illustrated in Table 11.

TABLE 11

Color deposition of compounded henna dye concentrate on human hair in shampoo (pH 4.5-3.0).

| Type of co-solvent | Propylene Glycol | Glycerin | Propanediol | Glycerin/ Propanediol 50:50 | Butilene Glycol |
|---|---|---|---|---|---|
| Dye + Lactic 0.1-5.0% | Light Yellow | Dark Yellow | Light Yellow | Dark Yellow | Dark Yellow |
| Dye + Glycolic 0.1-5.0% | Light Yellow | Dark Yellow | Light Yellow | Dark Yellow | Light Yellow |
| Dye + Acetic 0.1-5.0% | Low to none | Light Yellow | Light Yellow | Light Yellow | Low to none |

As it follows from Table 11, in the presence of co-solvent, such as Glycerin and Propanediol, golden, golden-orange, and dark golden shades can be obtained by heating compounded henna dye concentrate at low pH (4.5 and lower).

Most importantly, the co-solvent can be natural and made from renewable sources (Glycerin and corn based Propanediol).

Most surprising and unexpected was a significant color deposition from formulations prepared with this concentrate type even without presence of ligand binding complexes.

More Detailed Description of Preparation and Application of Natural Dye Concentrates in all Natural Permanent and Semi-Permanent Hair Dying Formulations Using dye concentrates oppose to mixing dry powders has significant technological advantages.

First, using dye concentrates in comparison with addition of compounded henna powders makes entire technological process more flexible. For example, same dye concentrate can be used for several formulation types, i.e. gels, emulsions, suspensions, shampoos and conditioners.

Second, it is known that some of the commonly used natural hair colorants like henna are not water soluble. In fact, main disadvantages of regular dry henna is required mixing of dry henna powder with boiling water to produce henna paste for application and application of heat for several hours.

Third, it is known that plant based extracts are inconsistent in concentration of their dyeing substances due to cultivar and environmental differences. Therefore, there are many challenges in shade consistency from batch to batch and variability of natural coloring formulations.

These problems can be worked out by using dye concentrates prepared as slurry of plant extracts in glycerin and/or glycol at low pH (4.0-2.5) and used for many formulations of permanent and semi-permanent color, emulsions, suspensions, shampoos and conditioners and stored for long periods of time without risk of running bacterial growth. This will also enable the greater technological flexibility and time saving in color adjusting.

Preparation of Dye Concentrates

Dye concentrates can be prepared using natural dye co-solvents, natural dye carriers, natural acids, henna, natural dyes and color contained actives, vitamins, co-enzymes, bioflavonoids, flavonoids, isoflavonoids, neoflavonoids.

Natural dye co-solvents can be selected from Glycerin and/or corn based Propanediol at concentration 5.0-50%.

Natural dye carriers can be selected from natural Benzyl Alcohol, natural Benzaldehyde and/or natural Benzyl Acetate at concentration 0.1-10%.

Natural acids can be selected from Lactic, Glycolic, Acetic or Citric acids at concentration 0.1-10.0%.

Henna can be used at concentration 0.1-30.0%.

Natural Dyes and Color Contained Actives (antioxidants, antimicrobials and other phyto-therapeuticals) can be used at concentration 0.5-15.0% and selected from: Acacia Dealbata Flower/Stem Extract, Annatto, Anthocyanins, Astaxanthin, Betanin, Capsanthin/Capsorubin, Carotenoids, Chlorophyll, Coptis Japonica Rhizome Extract, Crocus Sativus Flower Extract, Curcuma Longa, Turmeric Extract, Dunaliella Bardawil Powder, Gardenia Florida Fruit Extract, Gardenia Jasminoides Fruit Extract, Guaiazulene, Carthamin, Rosa Hybrid Flower Extract, Rubia Cordifolia Root Extract, Rubia Tinctorum Root Extract, Purpuroxanthin, Morindanigrin, Morindadiol, Rhubarb Extract, Purpurin, Pseudupururin, Morindone, Emodin, Crocin, Crocetin, Canthaxanthin, Sorghum Vulgare Seed/Skin/Stalk Extract, Vitis Vinifera (Grape) Fruit Powder, Vitis Vinifera (Grape) Skin Extract, Wine Extract, Deoxysantalin, Atromentin, Humin, Berberine.

Vitamins and Co-enzymes can be used at concentration 0.5-15.0% and selected from: Beta Carotene, D-Alpha Tocopherols, Co Enzyme Q-10, D-Biotin, Folic Acid, Niacin, Niacinamid, Riboflavin, Tocopherol, Vitamin A, B1, B2, B5, B6, B12, D3.

Bioflavonoids, flavonoids, isoflavonoids, neoflavonoids can be used at concentration 0.5-15.0% and selected from: Flavone, Luteolin, Apigenin, Baicalein, Rutin, Acacetin, Fisetin, Kaempferol, Myricetin, Quercetin, Naringenin, Hesperidin, Taxifolin, Genistein, Genistin, Daidzein, BiochaninA, Doxorubicin, Quercetin, Kaempferol, Myricetin, Fisetin, Isorhamnetin, Pachypodol, Rhamnazin, Eriodictyol, Homoeriodictyol, Tangeritin, Dihydrokaempferol, Glycitein, Catechins, Epicatechins, Morin, Brazelin, Brazilein, Haematein, Haematoxylon, Atrocappanon, Fukugetin, Datiscetin, Rhamnocitrin, Rhamnetin, Xanthorhamnin, Gossypetin.

Depending upon stability ingredients can be added together and heated up to 75 C or added after slurry cools down.

Total pH of dye concentrate should be 4.5 and lower.

Influence of Carriers.

A well known dye carrier is Benzyl Alcohol. Benzyl Alcohol, Benzaldehyde and Benzyl Acetate can be derived from sustainable sources like Jasmine, Ylang-Ylang, Cashew oil or oil of Bitter Almond. Other carriers from this category are Benzyl Benzoate or Ethyl Benzoate.

TABLE 12 comparative properties of potential dye carriers on "Dark Brown Henna"

| Acid type vs. carrier | Benzyl Acetate Natural | Benzyl Alcohol Natural/ Synthetic | Ethyl Benzoate | Benzaldehyde Natural | Benzyl Benzoate |
|---|---|---|---|---|---|
| Lactic | Light Brown | Dark Brown | Light Brown | Dark Brown | Light Brown |
| Glycolic | Light Brown | Dark Brown | Light Brown | Dark Brown | Light Brown |
| Acetic | Light Brown | Medium Brown | Low to none | Medium Brown | Low to none |

As shown in Table 12 both natural and synthetic dye carriers perform adequately well in this dye system. In fact, Benzyl Alcohol was unexpectedly found to be a superior dye carrier.

Distribution of Copper in the Hair Fiber and Cumulative Effect of Color.

It was noted that hair colorant prepared with copper based compounded henna formulations have a cumulative effect. This effect is probably due to particle distribution of copper ligand binded complexes in human hair. These poly-nucleus complexes form a stable structure with polymeric matrix with compensated spin and can disassociate to smaller formations and react with other ligands. Therefore, these complexes can act as a depot of ligands redistributing complex forming systems within an addition of more dye.

The best deposition of color was observed when an entire system was applied couple consecutive times without using durability of color. No "wash off" color has been observed. Therefore, it can be concluded that most of colorants had been cumulatively binded to the hair.

Hair Coloring Kits

An encapsulate free two part all plant based hair coloring kit with controlled color deposition due to delay in reaction between salt and dye was prepared. This product enables one to observe, control and adjust color development and deposition during the coloring process.

The product may be formulated as a kit which contains a cleaning solution that may preferably contain Citric Acid. The kit can contain customizable coloring tinctures, color adjusters, and root pretreatment solution for coverage of resistant gray.

Due to poly-nucleus copper complexes formations and reactions with other ligands, a cumulative effect of product can be achieved, even on the same day of application.

EXAMPLES

Example 1

Two Part Hair Coloring Kit

Two parts of Hair Coloring Kit and/or customizable coloring tinctures and/or root pretreatment solution for coverage of resistant gray Concentrations of ingredients will vary depending upon the type of the product (tincture, color, or solution for coverage of resistant gray). Same formula type makes these products highly versatile and compatible with each other. All percentages are by volume.

Part 1

| Component | Broad | Preferred | Most Preferred |
|---|---|---|---|
| DI Water to make 100% | 100% | | |
| Thickener (natural or synthetic) | 0.1 to 5.0% | 0.1 to 2.0% | 0.1 to 1.0% |
| Solvent (natural or synthetic) | 1.0 to 40.0% | 2 to 25.0% | 5 to 15.0% |
| Co-Solvent (natural or synthetic) | 0.1 to 20.0% | 1 to 15.0% | 3 to 10.0% |
| Surfactant | 0.1 to 10.0% | 1 to 10.0% | 2 to 5.0% |
| Carrier (natural or synthetic) | 0.1 to 10.0% | 1 to 10.0% | 2 to 5.0% |
| Acid (natural or synthetic) | 0.1 to 10.0% | 1 to 7.0% | 1 to 3.0% |
| Poly-nucleus copper based mineral complex (added to make part 1) - | 0.1 to 20.0% | 1 to 15.0% | 2 to 10.0% |

Part 2

Compounded henna made with at least one of the ingredients from classes of ingredients described in the Scope of Invention (added to make part 2)—0.5 to 20.0%

Example 2

Two Part Hair Coloring Kit for Resistant Gray

All Natural two part Hair Coloring Kit and/or customizable coloring tinctures and/or root pretreatment solution for coverage of resistant gray formulation:

| | Component | Broad Range | Preferred | Most Preferred |
|---|---|---|---|---|
| 1 | DI Water to make 100% | | | |
| 2 | Natural Thickener (selected from one or more of Guar Gum, Xanthan Gum, Hydroxyethylcellulose, Cellulose Gum) | 0.1 to 5.0% | 0.1 to 2.0% | 0.1 to 1.0% |

| | Component | Broad Range | Preferred | Most Preferred |
|---|---|---|---|---|
| 3 | Natural Solvent (selected from one or more of Natural Propanol, Natural Organic Ethanol, Natural Amyl Alcohol, Natural Butanol) | 1.0 to 40.0% | 2 to 25.0% | 5 to 15.0% |
| 4 | Natural Co-solvent (selected from one or more of Vegetable glycerin, Propanediol from corn) - | 0.1 to 20.0% | 1 to 15.0% | 3 to 10.0% |
| 5 | Natural Surfactant (selected from one or more of Decyl Glucoside, Coco Glucoside etc) | 0.1 to 10.0% | 1 to 10.0% | 2 to 5.0% |
| 6 | Natural Carrier (selected from one or more of Benzaldehyde from oil of Bitter Almond, Benzyl Acetate and Benzyl Alcohol from Jasmine or Ylang Ylang) | 0.1 to 10.0% | 1 to 10.0% | 2 to 5.0% |
| 7 | Natural Acid (selected from one or more of lactic, glycolic, acetic) to pH 4.5 and lower | 0.1 to 10.0% | 1 to 7.0% | 1 to 3.0% |
| 8 | Poly-nucleus copper based mineral complex (one part of salt is made from plant) - for part 1 at pH 4.5 and lower | 0.1 to 20.0% | 1 to 15.0% | 2 to 10.0% |
| | All Natural henna based vegetable dye composition - for part2 | | 0.5 to 20.0% | |

Examples of the above hair coloring kit with controlled color deposition due to delay in reaction between salt and dye applications:

In a separate two part all natural hair coloring kit embodiment of the invention, one part is applied on top of the other. When second part is applied, it is possible to observe, control, and adjust the development of color due to delay in reaction between salt and dye.

Optionally, the kit can be equipped with customizable coloring tinctures of tonal colors and sprays for resistant gray. Optionally, the kit can be applied few times on the same day to achieve cumulative properties.

In a mixable two part all natural hair coloring kit embodiment, parts can be mixed using conventional bowl and brush. When mixed parts are applied, it is possible to observe, control, and adjust the development of color due to delay in reaction between salt and dye. Optionally, the kit can be equipped with customizable coloring tinctures of tonal colors and sprays for resistant gray. Optionally, the kit can be applied few times on the same day to achieve cumulative properties.

In a shakable two part all natural hair coloring kit with applicator for home use embodiment, the parts can be mixed using conventional bowl and brush. When mixed parts are applied, it is possible to observe, control, and adjust the development of color due to delay in reaction between salt and dye. Optionally, the kit can be equipped with customizable coloring tinctures of tonal colors and sprays for resistant gray. Optionally, the kit can be applied few times on the same day to achieve cumulative properties.

One Part Dual Chamber Bottle Two Part All Natural Hair Coloring Kit.

Parts are mixed upon release. The kit can optionally contain customizable coloring tinctures of tonal colors mixable and/or as a part of one of the chambers of Dual Chamber bottle. Optionally, the kit can be equipped with customizable coloring spray for resistant gray. Optionally, the kit can be applied few times on the same day to achieve cumulative properties.

All Natural Kit for Blending Gray.

All Natural Kits for Blending Gray can be comprised of shampoo, conditioner, styling aid and color fixative spray and/or other delivery combination containing at least two of the above. This system is encapsulate free. Due to poly-nucleus copper complexes formations and reactions with other ligand, the cumulative effect of product can be achieved, even on the same day of application.

The color and grey coverage can be adjusted to desirable tone. At least one part will contain poly-nucleus copper based mineral complex. Another part contains compounded henna complex.

Formulation:
Shampoo
DI Water
Primary surfactant
Secondary surfactant
Tertiary Surfactant
Thickener
Solvent
Co-Solvent
Acid
Dye Carrier
Conditioning agents
Poly-nucleus copper based mineral complex or compounded henna complex
Conditioner
DI Water
Primary emulsifiers
Co-emulsifier
Thickeners
Oils
Solvent
Co-Solvent
Poly-nucleus copper based mineral complex or compounded henna complex
Conditioning agents
Acid
Spray
DI Water
Solvent
Co-solvent
Hair fixative resin
Poly-nucleus copper based mineral complex or compounded henna complex
Conditioning agents
Acid
Optionally may also contain:
Primary emulsifiers
Co-emulsifier
Thickeners
Formulation of All Natural Kit for Blending Grey.
Natural Shampoo

| | Component | Broad Range | Preferred | Most Preferred |
|---|---|---|---|---|
| 1 | DI Water to | 100% | Add to 100% | Add to 100% |
| 2 | Natural Thickener- Guar Gum | 0.1 to 5.0% | 0.1 to 2.0% | 0.1 to 1.0% |
| 3 | Natural solvent- Natural Propyl Alcohol | 0.1 to 10.0% | 1 to 8.0% | 2 to 5.0% |
| 4 | Natural co-solvent- Propanediol (from corn) | 0.1 to 10.0% | 1 to 8.0% | 2 to 5.0% |
| 5 | Natural Primary surfactant - selected from one or more of Sodium Cocoyl Isethionate, Sodium Lauroamphoacetate, Sodium Methyl Cocoyl Taurate, Methylisothiazolione | 1.0 to 20.0% | 2 to 18.0% | 12 to 15.0% |
| 5a | Natural Secondary surfactant- Decyl Glucoside | 1.0 to 15.% | 2 to 12.0% | 5 to 10.0% |
| 5b | Natural Tertiary surfactant - Cocamidopropyl Betaine | 1.0 to 5.0% | 2 to 12.0% | 5 to 10.0% |
| 6 | Natural dye carrier- natural benzaldehyde | 0.1 to 15.0% | 2 to 12.0% | 3 to 8.0% |
| 7 | Natural Citric Acid to pH 4.5 and lower | 0.1 to 10.0% | 0.2 to 5.0% | 0.5 to 3.0% |
| 8 | Poly-nucleus copper based mineral complex or compounded henna complex at pH 4.5 and lower | 0.1 to 20.0% | 1 to 15.0% | 2 to 10.0% |
| 40 | Natural conditioning agents- selected from one or more of Hydroxypropyl Guar & Chitosan Succinamide | 0.1 to 5.0% | 0.5 to 5.0% | 1 to 3.0% |

Natural Conditioner

| | Component | Broad Range | Preferred | Most Preferred |
|---|---|---|---|---|
| 1 | DI Water to make 100% | | Add to 100% | Add to 100% |
| 2 | Thickeners- selected from one or more of Guar gum, Xanthan gum, Hydroxyethyl Cellulose, Cellulose Gum | 0.1 to 5.0% | 0.1 to 2.0% | 0.1 to 1.0% |
| 3 | Solvent- Organic Grain Ethanol | 0.1 to 10.0% | 1 to 8.0% | 2 to 5.0% |
| 4 | Co-Solvent- Vegetable Glycerin | 0.1 to 10.0% | 1 to 8.0% | 2 to 5.0% |
| 7 | Natural Acid- Natural Citric Acid to pH 4.5 and lower | 0.1 to 10.0% | 0.2 to 5.0% | 0.5 to 2.0% |
| 8 | Poly-nucleus copper based mineral complex or compounded henna complex at pH 4.5 and lower | 0.1 to 20.0% | 1 to 15.0% | 2 to 10.0% |
| 17 | Oils-: selected from one or more of *Persea Gratissima* (Avocado) Oil; *Glycine Soja* Protein (Soybean); *Simmondsia Chinensis* (Jojoba) Seed Oil | 1.0 to 25.0% | 2.0 to 15.0% | 7.0 to 10.0% |
| 30 | Natural Primary emulsifiers- selected from one or more of Cetearyl Alcohol and Behenyl Alcohol | 0.5 to 10.0% | 1.0 to 8.0% | 2.0 to 7.0% |
| 31 | Co-emulsifier- selected from one or more of Arachidyl Glucoside, Coco Glucoside and Coconut Alcohol | 0.5 to 10.0% | 1.0 to 8.0% | 2.0 to 7.0% |
| 40 | Natural Conditioning agents- selected from one or more of Beta-Glucan, Hydroxypropyl Guar, Chitosan Succinamide, *Triticum Vulgare* (Hydrolyzed Wheat) Protein | 1.0 to 15.0% | 0.5 to 5.0% | 1 to 3.0% |

Natural Spray/Natural Styling Aid (Gel or Mousse)

| | Component | Broad Range | Preferred | Most Preferred |
|---|---|---|---|---|
| 1 | DI Water to make 100% | | Add to 100% | Add to 100% |
| 3 | Solvents- selected from one or more of Organic Grain Ethanol and Natural Propyl Alcohol | 0.1 to 45.0% | 5 to 30.0% | 5 to 15.0% |
| 4 | Co-solvents- Vegetable glycerin and Propanediol (from corn) | 0.1 to 15.0% | 1 to 12.0% | 2 to 5.0% |
| 7 | Natural Acid- Natural Citric acid to pH 4.5 and lower | 0.1 to 10.0% | 0.2 to 5.0% | 0.5 to 3.0% |

-continued

| Component | Broad Range | Preferred | Most Preferred |
|---|---|---|---|
| 8 Poly-nucleus copper based mineral complex or compounded henna complex at pH 4.5 and lower | 0.1 to 20.0% | 1 to 15.0% | 2 to 10.0% |
| 10 Conditioning agents- selected from one or more of Hydroxypropyl Guar & Chitosan Succinamide | 0.1 to 15.0% | 0.5 to 5.0% | 1 to 3.0% |
| 21 Hair fixative resins- selected from one or more of Guar Gum, Hyrdoxyethyl Cellulose, and Cellulose Gum | 0.1 to 5.0% | 0.1 to 2.0% | 0.1 to 1.0% | where each of the components of the kit may optionally contain:

| | | |
|---|---|---|
| 2 | Thickeners- selected from one or more of Guar gum, Xanthan gum, Hydroxyethyl Cellulose, Cellulose Gum | 0.1 to 5.0% |
| 30 | Natural Primary emulsifiers- selected from one or more of Cetearyl Alcohol and Behenyl Alcohol | 0.5 to 10.0% |
| 31 | Co-emulsifier- selected from one or more of Arachidyl Glucoside, Coco Glucoside and Coconut Alcohol | 0.5 to 10.0% |

Two part all natural kit for blending gray. At least one part should be conditioner, and another part can be shampoo or spray. On a course of application, it is possible to observe, control, and adjust the development of color due to cumulative effect. Application can be stopped when desirable blending of gray is achieved. After that kit can be continued once a week as maintenance.

Three parts all natural kit for blending gray. This system contains shampoo, conditioner, and spray. On a course of application, it is possible to observe, control, and adjust the development of color due to cumulative effect. Application can be stopped when desirable blending of gray is achieved. After that kit can be continued once a weak as maintenance.

Four parts all natural kit for blending gray. This system contains shampoo, conditioner, spray, and hair fixative aid. On a course of application, it is possible to observe, control, and adjust the development of color due to cumulative effect. Application can be stopped when desirable blending of gray is achieved. After that kit can be continued once a weak as maintenance.

Dual Chamber bottle all natural kit for blending gray. This system contains shampoo, conditioner, spray, and hair fixative aid. Either two or four parts are in Dual Chamber. Therefore, this kit can contain one dual chamber bottle with shampoo and conditioner combined with color fixative spray and hair fixative aid. Another combination is two dual chamber bottles—one contains shampoo and conditioner, and another contains hair fixative liquid and styling aid. On a course of application, it is possible to observe, control, and adjust the development of color due to cumulative effect. Application can be stopped when desirable blending of gray is achieved. After that kit can be continued once a weak as maintenance.

All Natural Tonal (Semi-Permanent) Tint Kit.

All Natural Tonal(Semi-Permanent) Tint Kits can be comprised of shampoo, conditioner, styling aid and color fixative spray and/or other delivery combinations containing at least two of the above. This product is encapsulate free. This system provides controlled color deposition. This applications enables to observe, control and adjust color development and deposition during the coloring process.

Due to poly-nucleus copper complexes formations and reactions with other ligand, a cumulative effect of product can be achieved, even on the same day of application. At least one part will contain poly-nucleus copper based mineral complex. Another part will contain compounded henna complex.

Formulation:

Shampoo
DI Water
Primary surfactant
Secondary surfactant
Tertiary Surfactant
Thickener
Solvent
Co-Solvent
Acid
Dye Carrier
Conditioning agents
Poly-nucleus copper based mineral complex or compounded henna complex Conditioner
DI Water
Primary emulsifiers
Co-emulsifier
Thickeners
Oils
Solvent
Co-Solvent
Poly-nucleus copper based mineral complex or compounded henna complex
Conditioning agents
Acid Spray
DI Water
Solvent
Co-solvent
Hair fixative resin
Poly-nucleus copper based mineral complex or compounded henna complex
Conditioning agents
Acid
Can also contain:
Primary emulsifiers
Co-emulsifier
Thickeners Formulation of All Natural Tonal (Semi-Permanent) Tint Kit:

Natural Shampoo

| | Component | Broad Range | Preferred | Most Preferred |
|---|---|---|---|---|
| 1 | DI Water to make100% | | Add to 100% | Add to 100% |
| 2 | Natural Thickener- Guar Gum | 0.1 to 5.0% | 0.1 to 2.0% | 0.1 to 1.0% |
| 3 | Natural solvent- Natural Propyl Alcohol | 0.1 to 10.0% | 1 to 8.0% | 2 to 5.0% |
| 4 | Natural co-solvent- Propanediol (from corn) | 0.1 to 10.0% | 1 to 8.0% | 2 to 5.0% |
| 5 | Natural Primary surfactant - selected from one or more of Sodium Cocoyl Isethionate, Sodium Lauroamphoacetate, Sodium Methyl Cocoyl Taurate, Methylisothiazolione | 1.0 to 20.0% | 2 to 18.0% | 12 to 15.0% |
| 5a | Natural Secondary surfactant- Decyl Glucoside | 1.0 to 15.% | 2 to 12.0% | 5 to 10.0% |
| 5b | Natural Tertiary surfactant - Cocamidopropyl Betaine | 1.0 to 5.0% | 2 to 5.0% | 3 to 5.0% |
| 6 | Natural dye carrier- natural benzaldehyde | 0.1 to 15.0% | 2 to 12.0% | 3 to 8.0% |
| 7 | Natural Citric Acid to pH 4.5 and lower | 0.1 to 10.0% | 0.2 to 5.0% | 0.5 to 3.0% |
| 8 | Poly-nucleus copper based mineral complex or compounded henna complex at pH 4.5 and lower | 0.1 to 20.0% | 1 to 15.0% | 2 to 10.0% |
| 10 | Natural conditioning agents- selected from one or more of Hydroxypropyl Guar & Chitosan Succinamide | 0.1 to 5.0% | 0.5 to 5.0% | 1 to 3.0% |

Natural Conditioner

| | Component | Broad Range | Preferred | Most Preferred |
|---|---|---|---|---|
| 1 | DI Water to make 100% | | | |
| 2 | Thickeners- selected from one or more of Guar gum, Xanthan gum, Hydroxyethyl Cellulose, Cellulose Gum | 0.1-5.0% | 0.1 to 2.0% | 0.1 to 1.0% |
| 3 | Solvent- Organic Grain Ethanol | 0.1-10.0% | 1 to 8.0% | 2 to 5.0% |
| 4 | Co-Solvent- Vegetable Glycerin | 0.1-10.0% | 1 to 8.0% | 2 to 5.0% |
| 7 | Natural Acid- Natural Citric Acid to pH 4.5 and lower | 0.1 to 10.0% | 0.2 to 5.0% | 0.5 to 2.0% |
| 8 | Poly-nucleus copper based mineral complex or compounded henna complex at pH 4.5 and lower | 0.1-20.0% | 1 to 15.0% | 2 to 10.0% |
| 10 | Natural Conditioning agents- selected from one or more of Beta-Glucan, Hydroxypropyl Guar, Chitosan Succinamide, *Triticum Vulgare* (Hydrolyzed Wheat) Protein | 1.0 to 15.0% | 0.5 to 5.0% | 1 to 3.0% |
| 13 | Natural Primary emulsifiers- selected from one or more of Cetearyl Alcohol and Behenyl Alcohol | 0.5-10.0% | 1.0 to 8.0% | 2.0 to 7.0% |
| 14 | Co-emulsifier- selected from one or more of Arachidyl Glucoside, Coco Glucoside and Coconut Alcohol | 0.5-10.0% | 1.0 to 8.0% | 2.0 to 7.0% |
| 17 | Oils- : selected from one or more of *Persea Gratissima* (Avocado) Oil; *Glycine Soja* Protein (Soybean); *Simmondsia Chinensis* (Jojoba) Seed Oil | 1.0-25.0% | 2.0 to 15.0% | 7.0 to 10.0% |

Natural Spray/Natural Styling Aid (Gel or Mousse)

| | Component | Broad Range | Preferred | Most Preferred |
|---|---|---|---|---|
| 1 | DI Water to make | 100% | Add to 100% | Add to 100% |
| 3 | Solvents- selected from one or more of Organic Grain Ethanol and Natural Propyl Alcohol | 0.1 to 45.0% | 5 to 30.0% | 5 to 15.0% |
| 4 | Co-solvents- selected from one or more of Vegetable glycerin and Propanediol (from corn) | 0.1 to 15.0% | 1 to 12.0% | 2 to 5.0% |
| | Hair fixative resins- selected from one or more of Guar Gum, Hyrdoxyethyl Cellulose, Cellulose Gum | 0.1 to 5.0% | 0.2 to 5.0% | 0.5 to 3.0% |

-continued

| Component | Broad Range | Preferred | Most Preferred |
|---|---|---|---|
| Conditioning agents- selected from one or more of Hydroxypropyl Guar & Chitosan Succinamide | 0.1 to 15.0% | 0.5 to 5.0% | 1 to 3.0% |
| 7 Natural Acid- Natural Citric acid to pH 4.5 and lower | 0.1-10.0% | 0.2 to 5.0% | 0.5 to 3.0% |
| 8 Poly-nucleus copper based mineral complex or compounded henna complex at pH 4.5 and lower | 0.1-20.0% | 1 to 15.0% | 2 to 10.0% |

Where each of the above compositions may also optionally contain:

| | | |
|---|---|---|
| | Natural Primary emulsifiers - selected from one or more of Cetearyl Alcohol and Behenyl Alcohol | 0.5 to 10.0% |
| | Co emulsifier - selected from one or more of Arachidyl Glucoside, Coco Glucoside and Coconut Alcohol | 0.5 to 10.0% |
| 2 | Thickeners - selected from one or more of Guar gum, Xanthan Gum, Hydroxyethyl Cellulose, Cellulose Gum | 0.1 to 5.0% |

Kit Embodiments:

In a preferred embodiment a two part All Natural Tonal (Semi-Permanent) Tint Kit system delivers coloring tone and/or can be applied on its own as a semi-permanent color. At least one part should be conditioner, and another part can be shampoo or spray. Over a course of application, it is possible to observe, control, and adjust the development of color due to the cumulative effect. The application can be stopped when a desirable blending of gray is achieved. After that, the kit can be continued once a week as maintenance.

In a preferred embodiment a three part All Natural Tonal (Semi-Permanent)Tint Kit system delivers coloring tone and/or can be applied on its own as a semi-permanent color. This system contains shampoo, conditioner, and spray. Over a course of application, it is possible to observe, control, and adjust the development of color due to the cumulative effect. The application can be stopped when a desirable blending of gray is achieved. After that, the t kit can be continued once a week as maintenance.

In a preferred embodiment a four part All Natural Tonal (Semi-Permanent)Tint Kit system delivers coloring tone and/or can be applied on its own as a semi-permanent color. This system contains shampoo, conditioner, spray, and hair fixative aid. Over a course of application, it is possible to observe, control, and adjust the development of color due to the cumulative effect. The application can be stopped when a desirable blending of gray is achieved. After that, the kit can be continued once a week as maintenance.

All Natural Tonal (Semi-Permanent)Tint Kit may be comprised of dual chamber bottles that deliver coloring tone and/or can be applied on its own as a semi-permanent color. This system contains shampoo, conditioner, spray, and hair fixative aid. Either two or four parts are in the dual chambers. Therefore, this kit can contain one dual chamber bottle with shampoo and conditioner combined with color fixative spray and hair fixative aid. In another embodiment, the combination is two dual chamber bottles—one contains shampoo and conditioner, and another contains hair fixative liquid and styling aid. Over a course of application, it is possible to observe, control, and adjust the development of color due to the cumulative effect. Application can be stopped when a desirable blending of gray is achieved. After that kit can be continued once a week as maintenance.

We claim:

1. A two part composition for dyeing keratin fibers, comprising a copper compound, and a color delivering ingredient selected from the group consisting of natural dyes, color contained actives, vitamins, co-enzymes, bioflavonoids, flavonoids, isoflavonoids, neoflavonoids, and combinations of two or more thereof, at a pH of 4.5 or less, wherein the color contained actives are selected from the group consisting of antioxidants, antimicrobials, phyto-therapeuticals, and combinations of two or more thereof.

2. The composition of claim 1 where the copper compound is selected from the group consisting of copper lactate, copper gluconate, copper acetate, copper glycinate, copper acetate, copper lysine, copper tartrate, copper salicylate, copper succinate, and combinations of two or more thereof.

3. The composition of claim 1 wherein the color delivering ingredient is a natural dye selected from the group consisting of henna, acacia dealbata flower extract, acacia dealbata stem extract, annatto, anthocyanins, astaxanthin, betanin, capsanthin/capsorubin, carotenoids, chlorophyll, coptis japonica rhizome extract, crocus sativus flower extract, curcuma longa, turmeric extract, dunaliella bardawil powder, gardenia florida fruit extract, gardenia jasminoides fruit extract, guaiazulene, carthamin, rosa hybrid flower extract, rubia cordifolia root extract, rubia tinctorum root extract, purpuroxanthin, morindanigrin, morindadiol, rhubarb extract, purpurin, pseudupururin, morindone, emodin, crocin, crocetin, canthaxanthin, sorghum vulgare seed extract, sorghum vulgare skin extract, sorghum vulgare stalk extract, vitis vinifera (grape) fruit powder, vitis vinifera (grape) skin extract, wine extract, deoxysantalin, atromentin, humin, berberine, and combinations of two or more thereof.

4. The composition of claim 1 where the color delivering ingredient is a vitamin selected from the group consisting of Beta Carotene, D-Alpha Tocopherols, D-Biotin, Folic Acid, Niacin, Niacinamid, Riboflavin, Tocopherol, Vitamin A, B1, B2, B5, B6, B12, D3, and combinations of two or more thereof.

5. The composition of claim 1 where the color delivering ingredient is selected from the group consisting of bioflavonoids, flavonoids, isoflavonoids, neoflavonoid, and combinations of two or more thereof.

6. The composition of claim 1, further comprising a mineral salt selected from the group consisting of Ferrous Lactate, Ferrous Gluconate, Ferrous Fumarate, Ferrous Citrate, Ferric Ammonia Citrate, Zinc Lactate, Zinc Citrate, Zinc Picolinate, Zinc Tartrate, Potassium Gluconate, Potassium Citrate, Potassium Lactate, Potassium Citrate, Potassium Succinate, Potassium Chloride, Calcium Maleate, Magnesium Citrate, Magnesium Carbonate, Magnesium Oxide, Calcium Gluconate, Calcium Citrate, Calcium Carbonate, Manganese Gluconate, Manganese Glycinate, Selenium Selenomethionine, and combinations of two or more thereof.

7. The composition of claim 1 where the natural dye is henna.

8. The composition of claim 1, wherein the color delivering ingredient is obtained from a natural source.

9. The composition of claim 1 where the pH is 4.0 to 4.5.

10. The composition of claim 7 where the henna is in the form of a concentrate made by mixing compounded henna with acid and natural co-solvent vegetable Glycerin, corn-derived Propanediol, and other natural glycols and poly-alcohols.

11. The composition of claim 1 where the composition comprises 2 parts added together before use, part 1 containing:
   (a) natural thickener, within a range of from about 0.1 to about 5.0%;
   (b) natural solvent, within the range of from about 1.0 to about 40.0%;
   (c) natural co-solvent, within a range of from about 0.1 to about 20.0%;
   (d) natural surfactant, within a range of from about 0.1 to about 10.0%;
   (e) natural carrier, within a range of from about 0.1 to about 10.0%;
   (f) natural acid, within the range of from about 0.1 to about 10.0% to a pH of less than or equal to about pH 4.5;
   (g) poly nucleus copper based mineral complex at pH 4.5 and lower;
   (h) DI water in a quantity sufficient to 100%; and
part 2 containing compounded henna, within a range of from about 0.5 to about 20.0% , made with at least one of the ingredients from the above classes of ingredients added to make part 2 at pH 4.5 and lower.

12. The composition of claim 1 where the composition comprises 2 parts added together before use, part 1 containing:
   (a) natural thickener, within a range of from about 0.1 to about 2.0%;
   (b) natural solvent, within the range of from about 2.0 to about 25.0%;
   (c) natural co-solvent, within a range of from about 1.0 to about 15.0%;
   (d) natural surfactant, within a range of from about 1.0 to about 10.0%;
   (e) natural carrier, within a range of from about 1.0 to about 10.0%;
   (f) natural acid, within the range of from about 1.0 to about 7.0% to a pH of less than or equal to about pH 4.5;
   (g) poly-nucleus copper based mineral complex, within a range of from about 1% to about 15% at pH 4.5 and lower;
   (h) DI water in a quantity sufficient to 100%; and
part 2 containing compounded henna, within a range of from about 0.5 to about 20.0% made with at least one of the ingredients from the above classes of ingredients added to make part 2 at pH 4.5 and lower.

13. The composition of claim 1 where the composition comprises 2 parts added together before use, part 1 containing:
   (a) natural thickener, within a range of from about 0.1 to about 1.0%;
   (b) natural solvent, within the range of from about 5.0 to about 15.0%;
   (c) natural co-solvent, within a range of from about 3.0 to about 10.0%;
   (d) natural surfactant, within a range of from about 2.0 to about 5.0%;
   (e) natural carrier, within a range of from about 2.0 to about 5.0%;
   (f) natural acid, within the range of from about 1.0 to about 3.0% to a pH of less than or equal to about pH 4.5;
   (g) poly-nucleus copper based mineral complex, within a range of from about 2% to about 10% at pH 4.5 and lower;
   (h) DI water in a quantity sufficient to 100%; and
part 2 containing compounded henna, within a range of from about 0.5% to about 20.0% , made with at least one of the ingredients from the above classes of ingredients added to make part 2 at pH 4.5 and lower.

14. The composition of claim 1 where the composition comprises 2 parts added together before use, part 1 containing:
   (a) a natural thickener selected from the group consisting of guar gum, xanthan gum, hydroxyethylcellulose, cellulose gum, and combinations of two or more thereof, within the range of from about 0.1 to about 5.0%;
   (b) a natural solvent selected from the group consisting of natural propanol, natural organic ethanol, natural amyl alcohol, natural butanol, and combinations of two or more thereof, within a range of from about 1.0 to about 40.0%;
   (c) a natural co-solvent selected from the group consisting of vegetable glycerin, corn-derived propanediol, and combinations thereof, within the range of from about 0.1 to 20.0%;
   (d) a Natural Surfactant selected from the group consisting of decyl glucoside, coco glucoside, and combinations thereof, within a range of from about 0.1 to 10.0% (vv/);
   (e) a natural carrier selected the group consisting of benzaldehyde from oil of bitter almond, benzyl acetate and benzyl alcohol from Jasmine, benzyl acetate and benzyl alcohol from Ylang Ylang, and combinations of two or more thereof, within a range of from about 0.1 to about 10.0%;
   (f) a Natural Acid selected from the group consisting of lactic acid, glycolic acid, acetic acid, and combinations of two or more thereof, within a range of from about 0.1 to about 10%, to pH 4.5 and lower;
   (g) a poly-nucleus copper based mineral complex at pH 4.5 or lower, within a range of from about 0.1 to about 20%, wherein one part of salt is made from a plant;
   (h) DI water in a quantity sufficient to 100%; and
part 2 containing all Natural henna based vegetable dye composition within a range of from about 0.5 to about 20.0%.

15. The composition of claim 1 where the composition comprises 2 parts added together before use, part 1 containing:
   (a) natural thickener, within a range of from about 0.1 to about 2.0% , selected from the group consisting of guar gum, xanthan gum, hydroxyethylcellulose, cellulose gum, and combinations of two or more thereof;
   (b) a natural solvent, within a range of from about 2.0 to about 25.0%, selected from the group consisting of natural propanol, natural organic dthanol, natural amyl alcohol, natural butanol, and combinations of two or more thereof;
   (c) a natural co-solvent, within a range of from about 1.0 to about 15.0%, selected from the group consisting of vegetable glycerin, propanediol from corn, and combinations thereof;

(d) a natural surfactant, within a range of from about 1.0 to about 10.0%, selected from the group consisting of decyl glucoside, xoco glucoside, and combinations thereof;
(e) a natural carrier, within a range of from about 1.0 to about 10.0%, selected from the group consisting of benzaldehyde from oil of bitter almond, benzyl acetate and benzyl alcohol from Jasmine, benzyl acetate and benzyl alcohol from Ylang Ylang, and combinations of two or more thereof;
(f) a natural acid, within a range of from about 1.0 to about 7.0%, selected from the group consisting of lactic acid, glycolic acid, acetic acid and combinations of two or more thereof, to pH 4.5 and lower;
(g) a poly-nucleus copper based mineral complex, within a range of from about 1.0 to about 15.0%, wherein one part of salt is made from plant, at pH 4.5 and lower;
(h) DI Water in a quantity sufficient to make 100%; and
part 2 containing all natural henna based vegetable dye composition within a range of from about 0.5 to about 20.0%.

16. The composition of claim 1 where the composition comprises 2 parts added together before use, part 1 containing:
(a) natural thickener, within a range of from about 0.1 to about 10.0%, selected from the group consisting of guar gum, xanthan gum, hydroxyethylcellulose, cellulose gum, and combinations of two or more thereof;
(b) a natural solvent, within a range of from about 5.0% to about 15.0%, selected from the group consisting of natural propanol, natural organic ethanol, natural amyl alcohol, natural butanol, and combinations of two or more thereof;
(c) a natural co-solvent, within a range of from about 3.0% to about 10.0%, selected from the group consisting of vegetable glycerin, propanediol from corn, and combinations thereof;
(d) a natural surfactant, within a range of from about 2.0% to about 5.0%, selected from the group consisting of decyl glucoside, coco glucoside, and combinations thereof;
(e) a natural carrier, within a range of from about 2.0% to about 5.0%, selected from the group consisting of benzaldehyde from oil of bitter almond, benzyl acetate and benzyl alcohol from Jasmine, benzyl acetate and benzyl alcohol from Ylang Ylang, and combinations of two or more thereof;
(f) a natural acid, within a range of from about 1.0 to about 3.0%, selected from the group consisting of lactic acid, glycolic acid, acetic acid and combinations of two or more thereof, to pH 4.5 and lower;
(g) a poly-nucleus copper based mineral complex, within a range of from about 2.0 to about 10.0%, wherein one part of salt is made from plant, at pH 4.5 and lower;
(h) DI Water in a quantity sufficient to make 100%; and
part 2 containing all Natural henna based vegetable dye composition, within a range of from about 0.5 to about 20.0%.

17. An all natural system for blending gray comprising at least two of shampoo, conditioner, natural spray/natural styling aid, wherein the natural spray/styling aid is a gel or mousse,
wherein the natural shampoo comprises:
(a) a guar gum natural thickener in a range of from about 0.1 to about 5.0%;
(b) a natural propyl alcohol natural solvent in a range of from about 0.1 to about 10.0%;
(c) corn-derived propanediol natural co-solvent in a range of from about 0.1 to about 10.0%;
(d) a natural primary surfactant selected from the group consisting of sodium cocoyl isethionate, sodium lauroamphoacetate, sodium methyl cocoyl taurate, methylisothiazolione, and combinations of two or more thereof, in a range of from about 1.0 to about 20.0%;
(e) a decyl-glucoside natural secondary surfactant in a range of from about 1.0 to about 15.0%;
(f) a cocamidopropyl betaine natural tertiary surfactant in a range of from about 1.0 to about 5.0%;
(g) a natural benzaldehyde natural dye carrier in a range of from about 0.1 to about 15.0%;
(h) natural citric acid in a range of from about 0.1 to about 10.0%, to pH of 4.5 and lower;
(i) a complex in a range of from about 0.1 to about 20.0%, selected from the group consisting of poly-nucleus copper based mineral complex, compounded henna complex, and combinations thereof, at pH 4.5 and lower;
(j) a natural conditioning agent selected from hydroxypropyl guar, chitosan succinamide and combinations thereof, in a range of from about 0.1 to about 5.0%;
(k) DI water in a quantity sufficient to 100%;
wherein the natural conditioner comprises;
(a) a natural thickener selected from the group consisting of guar gum, xanthan gum, hydroxyethyl cellulose, cellulose gum, and combinations of two or more thereof, in a range of from about 0.1 to about 5.0%;
(b) an organic grain ethanol solvent in a range of from about 0.1 to about 10.0%;
(c) a vegetable glycerin co-solvent in a range of from about 0.1 to about 10.0%;
(d) citric acid natural acid in a range of from about 0.1 to about 10% to a pH of less than or equal to pH 4.5;
(e) a complex selected from a poly-nucleus copper based mineral complex, a compounded henna complex, or a combination thereof, at a pH 4.5 or less, in a range of from about 0.1 to about 20%;
(f) an oil selected from the group consisting of Persea Gratissima (avocado) oil, Glycine Soja protein (soybean) oil, Simmondsia Chinensis (jojoba) seed oil, and combinations of two or more thereof, in a range of from about 1.0 to about25%;
(g) a natural primary emulsifier selected from the group consisting of cetearyl alcohol, behenyl alcohol and combinations thereof, in a range of from about 0.5 to about 10%;
(h) a co-emulsifier selected from the group consisting of arachidyl glucoside, coco glucoside, coconut alcohol, and combinations of two or more thereof, in a range of from about 0.5 to about 10.0%;
(i) a natural conditioning agent selected from the group consisting of of beta-glucan, hydroxypropyl guar, chitosan succinamide, Triticum Vulgare (hydrolyzed wheat) protein, and combinations of two or more thereof in a range of from about 1.0 to about 15.0%;
(j) DI water in an amount sufficient to 100%; and
wherein the Natural Spray/Natural Styling Aid comprises;
(a) a solvent selected from the group consisting of organic grain ethanol, natural propyl alcohol, and combinations thereof in a range of from about 0.1 to about 45.0%;
(b) a co-solvent selected from vegetable glycerin, corn-derived propanediol, and combinations thereof, in a range of from about 0.1 to about 15.0%;
(c) natural citric acid in a range of from about 0.1 to about 10.0%, to pH 4.5 and lower;

(d) a complex selected from the group consisting of poly-nucleus copper based mineral complex, compounded henna complex, and combinations thereof, at pH 4.5 and lower, in a range of from about 0.1 to about 20.0%;
(e) a Conditioning agent selected from the group consisting of hydroxypropyl guar, chitosan succinamide, and combinations thereof, in a range of from about 0.1 to about 15.0%.
(f) a hair fixative resin selected from the group consisting of guar gum, hydroxyethyl cellulose, cellulose gum, and combinations of two or more thereof, in a range of from about 0.1 to about 5.0%;
(g) DI Water in a quantity sufficient to 100%.

18. An all natural system for blending gray comprising at least two of shampoo, conditioner, natural spray/natural styling aid, wherein the natural spray/natural styling aid is a gel or mousse, wherein the shampoo is a natural shampoo comprising;
(a) a guar gum natural thickener in a range of from about 0.1 to about 2.0%;
(b) a natural propyl alcohol natural solvent in a range of from about 1 to about 8.0%;
(c) a corn-derived propanediol natural co-solvent in a range of from about 1 to about 8.0%;
(d) a natural primary surfactant selected from the group consisting of sodium cocoyl isethionate, sodium lauroamphoacetate, sodium methyl cocoyl taurate, methylisothiazolione, and combinations of two or more thereof, in a range of from about 2 to about 18.0%;
(e) a decyl glucoside natural secondary surfactant in a range of from about 2 to about 12.0%;
(f) a cocamidopropyl betaine natural tertiary surfactant in a range of from about 2 to about 12.0%;
(g) a natural benzaldehyde natural dye carrier in a range of from about 2 to about 12.0%;
(h) natural citric acid to pH 4.5 and lower, in a range of from about 0.2 to about 5.0%;
(i) a complex selected from the group consisting of poly-nucleus copper based mineral complex, compounded henna complex, and combinations thereof, at pH 4.5 and lower, in range of from about 1 to about 15.0%;
(j) a natural conditioning agent selected from the group consisting of hydroxypropyl guar, chitosan succinamide, and combinations thereof, in a range of from about 0.5 to about 5.0%. (k) DI Water in quantity sufficient to 100%;

wherein the conditioner is a natural conditioner comprising:
(a) a thickener selected from the group consisting of guar gum, xanthan gum, hydroxyethyl cellulose, cellulose gum, and combinations of two or more thereof, in a range of from about 0.1 to about 2.0%;
(b) an organic grain ethanol solvent in a range of from about 1 to about 8.0%;
(c) a vegetable glycerin co-solvent in a range of from about 1 to about 8.0%;
(d) natural citric acid to pH 4.5 and lower in the range of from about 0.2 to about 5.0%;
(e) a complex selected from the group consisting of a poly-nucleus copper based mineral complex, a compounded henna complex, or a combination thereof at pH 4.5 and lower, in a range of from about 1 to about 15.0%;
(f) an oil selected from the group consisting of Persea Gratissima (avocado) oil, Glycine Soja Protein (soybean) oil, Simmondsia Chinensis (jojoba) seed oil, and combinations of two or more thereof, in a range of from about 2.0 to about 15.0%;
(g) a natural primary emulsifier selected from the group consisting of cetearyl alcohol, behenyl alcohol, and combinations thereof, in a range of from about 1.0 to about 8.0%;
(h) a co-emulsifier selected from the group consisting of arachidyl glucoside, coco glucoside, coconut alcohol, and combinations of two or more thereof, in a range of from about 1.0 to about 8.0%;
(i) a natural conditioning agent selected from the group consisting of beta-glucan, hydroxypropyl guar, chitosan succinamide, Triticum vulgare (hydrolyzed wheat) protein, and combinations of two or more thereof, in a range of from about 0.5 to about 5.0%;
(j) DI Water in quantity sufficient to 100%; and wherein the natural spray/natural styling aid comprises:
(a) a solvent selected from the group consisting of organic grain ethanol, natural propyl alcohol, and combinations thereof in a range of from about5 to about 30.0%;
(b) a co-solvent selected from the group consisting of vegetable glycerin, corn-derived propanediol, and combinations thereof in a range of from about 1 to about 12.0%;
(c) natural citric acid to pH 4.5 and lower, in a range of from about 0.2 to about 5.0%;
(d) a complex selected from poly-nucleus copper based mineral complex, compounded henna complex, and combinations thereof at pH 4.5 and lower, in a range of from about 1to about 15.0%;
(e) a conditioning agent selected from the group consisting of hydroxypropyl guar, chitosan succinamide, and combinations thereof, in a range of from about 0.5 to about 5.0%;
(f) a hair fixative resin selected from the group consisting of guar gum, hydroxyethyl cellulose, cellulose gum, and combination thereof, in a range of from about 0.1 to about 2.0%;
(g) DI Water in quantity sufficient to 100%.

19. An all natural system for blending gray comprising at least two of shampoo, conditioner, natural spray/natural styling aid, wherein the natural spray/natural styling aid is a gel or mouse;

wherein the shampoo is a natural shampoo comprising:
(a) a guar-gum natural thickener, in a range of from about 0.1 to about 1.0%;
(b) a natural propyl alcohol natural solvent in a range of from about 2 to about 5.0%;
(c) a corn-derived propanediol natural co-solvent, in a range of from about 2 to about 5.0%;
(d) a natural primary surfactant selected from the group consisting of sodium cocoyl isethionate, sodium lauroamphoacetate, sodium methyl cocoyl taurate, methylisothiazolione, and combinations of two or more thereof, in a range of from about 12 to about 15.0%;
(e) a decyl glucoside natural secondary surfactant in a range of from about 5 to about 10.0%;
(f) a cocamidopropyl betaine natural tertiary surfactant in a range of from about 5 to about 10.0%;
(g) a natural benzaldehyde Natural dye carrier in a range of from about 3 to about 8.0%;
(h) natural citric acid in a range of from about 0.5 to about 3.0% , and to pH 4.5 and lower;
(i) a complex selected from a poly-nucleus copper based mineral complex, a compounded henna complex, and combinations thereof, at pH 4.5 and lower, in a range of from about 2 to about 10.0%;

(j) a natural conditioning agent selected from the group consisting of hydroxypropyl guar, chitosan succinamide, and combinations thereof, in a range of from about 1 to about 3.0%;

(j) DI Water in a quantity sufficient to 100%;

wherein the conditioner is a natural conditioner comprising:

(a) a thickener selected from the group consisting of guar gum, xanthan gum, hydroxyethyl cellulose, cellulose gum, and combinations of two or more thereof, in a range of from about 0.1 to about 1.0%;

(b) an organic grain ethanol solvent in a range of from about 2 to about 5.0%;

(c) a vegetable glycerin co-solvent in a range of from about 2 to about 5.0%;

(d) natural citric acid in a range of from about 0.5 to about 2.0%, to pH 4.5 and lower;

(e) a complex selected from ap-nucleus copper based mineral complex, a compounded henna complex, and combinations thereof in a range of from about 2 to about 10%, at pH 4.5 and lower;

(f) an oil selected from the group consisting of Persea Gratissima (avocado) oil, glycine Soja protein (soybean) oil, Simmondsia Chinensis (jojoba) seed oil, and combinations of two or more thereof, in a range of from about 7.0 to about 10.0%;

(g) a natural primary emulsifier selected from the group consisting of cetearyl alcohol, behenyl alcohol, and combinations thereof, in a range of from about 2.0 to about 7.0%;

(h) a Co-emulsifier selected from the group consisting of arachidyl glucoside, coco glucoside, coconut alcohol, and combinations of two or more thereof, in a range of from about 2.0 to about 7.0%;

(i) a natural conditioning agent selected from the group consisting of beta-glucan, hydroxypropyl guar, chitosan succinamide, Triticum Vulgare (hydrolyzed wheat) protein, and combinations of two or more thereof, in a range of from about 1 to about 3.0%;

(j) DI Water in a quantity sufficient to 100%; and wherein the Natural Spray/Natural Styling Aid comprises:

(a) a solvent selected from organic grain ethanol, natural propyl alcohol, and combinations thereof, in a range of from about 5 to about 15.0%;

(b) a co-solvent selected from the group consisting of vegetable glycerin, corn-derived propanediol and combinations thereof, in a range of from about 2 to about 5.0%;

(c) natural citric acid in a range of from about 0.5 to about 3.0%, to pH 4.5 and lower;

(d) a complex selected from a poly-nucleus copper based mineral complex, a compounded henna complex, and combinations thereof, in a range of from about 2 to about 10.0%, at pH 4.5 and lower;

(e) a conditioning agent selected from the group consisting of hydroxypropyl guar, chitosan succinamide, and combinations thereof, in a range of from about 1 to about 3.0%

(f) a hair fixative resin selected from the group consisting of guar gum, hydroxyethyl cellulose, cellulose gum, and combinations of two or more thereof, in a range from about 0.1 to about 1.0%;

(g) DI Water in quantity sufficient to 100%.

20. The composition of claim 1, wherein the color delivering ingredient is a co-enzyme.

21. The composition of claim 20, wherein the co-enzyme is Co Enzyme Q 10.

22. The composition of claim 5, wherein the color delivering ingredient is selected from the group consisting of flavone, luteolin, apigenin, baicalein, rutin, acacetin, fisetin, kaempferol, myricetin, quercetin, naringenin, hesperidin, taxifolin, genistein, genistin, daidzein, biochanin A, doxorubicin, quercetin, kaempferol, myricetin, fisetin, isorhamnetin, pachypodol, rhamnazin, eriodictyol, homoeriodictyol, tangeritin, dihydrokaempferol, glycitein, catechins, epicatechins, morin, brazelin, brazilein, haematein, haematoxylon, atrocappanon, fukugetin, datiscetin, rhamnocitrin, rhamnetin, xanthorhamnin, gossypetin, and combinations of two or more thereof.

23. The all natural system of claim 17, wherein at least one of the shampoo, conditioner, and natural spray/natural styling aid, further comprises a component selected from the group consisting of thickeners, natural primary elmulsifiers, co-emulsifiers, and combinations of two or more thereof;

wherein the thickener is selected from the group consisting of guar gum, xanthan gum, hydroxyethyl cellulose, cellulose gum, and combinations of two or more thereof, in a range of from about 0.1 to about 5.0%;

wherein the natural primary emulsifier is selected from the group consisting of cetearyl alcohol, behenyl alcohol, and combinations thereof, in a range of from about 0.5 to about 10.0%; and wherein the co-emulsifier is selected from the group consisting of arachidyl glucoside, coco glucoside, coconut alcohol, and combinations of two or more thereof, in a range of from about 0.5 to about 10.0%.

24. The all natural system of claim 18, wherein at least one of the shampoo, conditioner, and natural spray/natural styling aid, further comprises a component selected from the group consisting of a thickener, a natural primary emulsifier, a co-emulsifier, and combinations of two or more thereof;

wherein the thickener is selected from the group consisting of guar gum, xanthan gum, hydroxyethyl cellulose, cellulose gum, an combinations of two or more thereof, in a range of from about 0.1 to about 5.0%;

wherein the natural primary emulsifier is selected from the group consisting of cetearyl alcohol behenyl alcohol, and combinations thereof, in a range of from about 0.5 to about 10.0%; and wherein the co-emulsifier is selected from the group consisting of arachidyl glucoside, coco glucoside, coconut alcohol, and combinations of two or more thereof in a range of from about 0.5 to about 10.0%.

25. The all natural system of claim 19, wherein at least one of the shampoo, conditioner, and natural spray/natural styling aid, further comprises a component selected from the group consisting of a thickener, a natural primary emulsifier, a co-emulsifier, and combinations of two or more thereof;

wherein the thickener is present within a range of from about 0.1 to about 5.0% and is selected from the group consisting of Guar gum, Xanthan gum, Hydroxyethyl Cellulose, Cellulose Gum, and combinations of two or more thereof;

wherein the natural primary emulsifier is present within a range of from about 0.5 to about 10.0%, and is selected from the group consisting of cetearyl alcohol, behenyl alcohol, and combinations thereof; and wherein the co-emulsifier is present within a range of from about 0.5 to about 10.0%, and is selected from the group consisting of arachidyl glucoside, coco glucoside, coconut alcohol, and combinations of two or more thereof.

* * * * *